United States Patent [19]

Tyszblat

[11] Patent Number: 4,772,436
[45] Date of Patent: Sep. 20, 1988

[54] PROCESS FOR THE PREPARATION OF A DENTAL PROSTHESIS BY SLIGHT SOLID PHASE FRITTING OF A METAL OXIDE BASED INFRASTRUCTURE

[76] Inventor: Michèle Tyszblat, 3 avenue Séverine, 92400 Courbevoie, France

[21] Appl. No.: 57,448

[22] Filed: Apr. 10, 1987

[30] Foreign Application Priority Data

Apr. 11, 1986 [EP] European Pat. Off. ........ 86400781.0

[51] Int. Cl.$^4$ ...................... A61C 5/10; A61C 13/083; B06B 3/00; C03C 17/02
[52] U.S. Cl. .......................................... 264/19; 65/33; 65/60.5; 65/60.8; 264/23; 433/223
[58] Field of Search ................ 433/214, 213, 60, 167, 433/222.1, 223, 202.1, 206, 207; 264/16-19, 23; 249/54; 425/2; 427/2; 65/33, 40, 42, 43, 60.5, 60.8, DIG. 11

[56] References Cited

U.S. PATENT DOCUMENTS

| | | | |
|---|---|---|---|
| 2,165,466 | 7/1939 | Erdle | 264/20 |
| 2,186,468 | 1/1940 | Schwartz | 264/19 |
| 2,227,770 | 1/1941 | Ungeweiss | 65/608 |
| 3,541,688 | 11/1970 | McLean et al. | 433/208 |
| 3,873,344 | 3/1975 | Church et al. | 65/60.5 |
| 4,040,844 | 8/1977 | Gnecco | |
| 4,155,964 | 5/1979 | Aronow | 264/19 |
| 4,562,882 | 1/1986 | Alleluia | 264/16 |
| 4,671,770 | 6/1987 | Bell et al. | 433/222.1 |

FOREIGN PATENT DOCUMENTS 216213 2/1908 Fed. Rep. of Germany .
1491042 1/1969 Fed. Rep. of Germany .
2129058 10/1972 France .
2291736 6/1976 France .
428088 7/1967 Switzerland .

OTHER PUBLICATIONS

"Current Status and Future of Ceramics in Dentistry", Ceramic Engineering and Science Proceedings, vol. 6, Jan./Feb. 1985, pp. 1-9, McLean.

*Primary Examiner*—Jan H. Silbaugh
*Assistant Examiner*—Karen D. Kutach
*Attorney, Agent, or Firm*—Cushman, Darby & Cushman

[57] ABSTRACT

A method for manufacturing a dental prosthesis from a shaped, slightly solid phase fritted metal oxide infrastructure whose pores are impregnated with a glass by molding a tooth model from a linearly expanding molding mass and contacting the model with a slip of metal oxide particles which particles are agglomerated onto the model. The agglomerated metal oxide particles forming an infrastructure which is shaped and baked to effect dehydration and withdrawal of the model from the infrastructure before the fritting and glass impregnation of the infrastructure.

29 Claims, No Drawings

PROCESS FOR THE PREPARATION OF A DENTAL PROSTHESIS BY SLIGHT SOLID PHASE FRITTING OF A METAL OXIDE BASED INFRASTRUCTURE

The present invention relates to a new method for manufacturing dental prostheses, as well as to prostheses obtained by this method.

Dental prostheses are generally defined as any part designed to be fitted onto the denture of a patient, for the purpose of restoring the denture to its natural shape, in whole or in part.

Hence, prostheses manufactured according to the present invention can comprise, for instance, peripheral caps or crowns that are placed on the stump of a natural tooth, or even prostheses that are generally designated as "inlay" or "onlay" which are indented to reconstitute a partial alteration of a tooth by filling a cavity, resulting from a loss of tooth substance, with a piece of the same form produced by the prosthesis, or even bridges, which are prostheses, that are supported simultaneously on the remaining parts of at least two teeth by compensating ultimately for one or several missing teeth.

Methods are known for manufacturing such prostheses which are most often metallic parts that are fusion molded, on which can be fixed, at a high temperature, an enamel which gives the prosthesis the appearance of a natural tooth.

These known prostheses exhibit the disadvantage of being delicate and costly to manufacture. Furthermore, because of their metallic content they are not entirely biocompatible, and a corrosion phenomenon of the prostheses has been observed which requires the replacement of the latter.

The present invention envisages the production of dental prostheses which are completely ceramic-based and which exhibit excellent mechanical characteristics which are comparable to those of natural teeth.

The prostheses which are manufactured in accordance with the present invention are biologically compatible with ceramics. They cost less to manufacture than known prostheses, and they can be fitted with great accuracy onto those parts of natural teeth where they are to be affixed.

It is known that "ceramics" are defined in the dental art not only as the products produced from terra cotta but also those which include enamels and metallic oxides such as aluminum oxide or zirconium oxide. "Ceramometallic prostheses" are those which are produced in part using metals that are generally found in the form of alloys.

The purpose of the present invention is to provide a method for manufacturing ceramic dental prostheses, characterized by the fact that a model of a tooth that is to receive the prosthesis is produced in a molding mass, such as plaster, which exhibits slight linear expansion during solidification; that a slip is prepared comprising a suspension in water of metal oxide particles such as aluminum oxide and/or zirconia, to which is added a suspension stabilization agent and optionally a pH control agent; that the model of the tooth previously produced is contacted with the slip so that the metal oxide particles aggregate on the surface of the model of the tooth, until a sufficient thickness is obtained; that there is imparted to the layer of metal oxides, the outer shape that is desired for the infrastructure of the prosthesis; that the model of the tooth coated with the metal oxide-based infrastructure is baked in order to effect initially dehydration of the model of the tooth which causes its withdrawal, at which point the solid phase of the metal oxide particles is slightly fritted; and that the infrastructure thus fritted is impregnated with glass at a temperature sufficient so that the glass occupies all of the open pores which exist in the infrastructure.

According to a preferred embodiment of the present invention, the outer surface of the prosthesis is coated with an enamel that is compatible with the nature of the glass used for impregnating the infrastructure and which has a coefficient of expansion close to that of the latter.

Thus, the method of the present invention comprises a first step of producing an infrastructure or skeleton which comprises an aggregation of metal oxide particles brought together by slight fritting in a solid phase and then in a second step, filling all of the existing interstices between the metal oxide particles with melted glass which completely fills the uninterrupted network of cavities left by the fritted metal oxide particles.

In other words, the prostheses according to the present invention are made by the total interlacing of two uninterrupted networks of which one comprises fine fritted metal oxide particles in the solid phase and the other comprises glass.

The dental prostheses obtained according to the present invention exhibit excellent mechanical features. Surprisingly, their mechanical features are indeed superior to those that can be obtained by complete fritting of metal oxide particles without impregnating them with glass.

The molding mass intended, in accordance with the present invention, for use in producing the model of the tooth, can be an alpha-type plaster comprising calcium sulfate hemihydrate, $CaSO_4.\frac{1}{2}H_2O$ without any mineral-based charge. This plaster must exhibit a linear solidification expansion (or setting), preferably, between 0.1% and 0.4%. This expansion increases with the quantity of plaster added to a given specific quantity of water in order to produce the molding. It also increases with the addition of sodium chloride (NaCl) or cellulose ether.

This molding mass can also comprise refractory charges such as silicon oxide or aluminum oxide, admixed with a binding agent, such as sodium silicate, ethyl silicate, ammonium sulfate, aluminum phosphate or sodium phosphate, or ammonium acid phosphate.

In accordance with the present invention, the molding mass for the model of the tooth must exhibit during its solidification a slightly linear expansion which can range, for instance, from 0.1% to 0.4%.

In a preferred embodiment of the present invention, the metal oxide employed comprises an alumina powder ($Al_2O_3$) which includes, optionally, in admixture a zirconium oxide ($ZrO_2$) powder in amounts that can be significant.

There can also be employed, in accordance with the present invention, zirconium oxide that is pure or that is stabilized with yttrium oxide.

The slip can be obtained according to the present invention, by placing, for instance, 100 g of metal oxide particles in about 12 to 20 g of water and by adding between 0.05 g and 0.5 g of a suspension stabilizing agent, which agent can comprise, for instance, a polyvinyl alcohol, an acrylic acid, a cellulose ester, or sodium silicate.

In accordance with the present invention it is also preferable to reduce the pH of the slip to an essentially neutral value, for instance, to a value of about 7 to 8, by the addition of an appropriate substance such as citric acid.

Before using the slip according to the invention, it is preferable to degas the latter, by subjecting it to ultrasonics in a receptacle where a vacuum is created.

In accordance with the present invention, the first baking of the infrastructure, made up of the layer of metal oxide particles applied onto the tooth model, has as its first goal the separation of those two elements by withdrawal of the molding mass that comprises the model of the tooth, which in the case of plaster is obtained by the loss of at least part of the constituent water of gypsum found in plaster.

Such dehydration of the plaster can be obtained by putting the infrastructure of metal oxide particles placed on the plaster model of the tooth inside an oven where the temperature is raised slowly, for instance about 1° C. per minute, until it reaches a temperature of about 180° C., then later in a more rapid manner up to about 330° C.

In this first heat treatment phase, the plaster separates from the powder metal oxide infrastructure.

In accordance with the present invention, a slight fritting of the metal oxide particles in a solid phase must be carried out so as to obtain a rigid skeleton, with open porosity, which is subjected during fritting to a slight withdrawal which is less, for example, than 0.4%, and which is compensated by the expansion that the model of the tooth undergoes during the solidification of the mass.

The present invention thus provides prostheses that adapt to the natural tooth with a great deal of accuracy.

In accordance with the present invention, it is advantageous for this fritting to be only a slight fritting, which simply produces a binding between the metal oxide particles without causing a substantial reduction of the infrastructure volume.

In accordance with the present invention, the heat treatment that makes it possible to attain the desired result, depends on its temperature, on the speed of temperature elevation, on the period of time during which the temperature is maintained and on the average size of the metal oxide particles.

Thus, for instance, for a heat treatment of about one to three hours, the temperature can be about 1050° C. to 1150° C. with metal oxide particles having an average size of about 3.5 microns.

The treatment temperature can be raised to 1250° C. with metal oxide particles having an average size of about 8.5 microns, and from 1300° C. to 1400° C. with metal oxide particles having an average size of about 20 microns.

The effect of an increase in the rate of temperature rise is the reduction of the withdrawal that occurs during fritting.

In accordance with the present invention, it is preferable not to use metal oxide particles which have too high a specific surface. Advantageously, there can be employed powders of metal oxide particles, having for instance, a specific surface of about 1 to 5 m$^2$ per g.

It is possible to raise the fritting temperature, while maintaining a slight withdrawal, by admixing with the aluminum oxide and/or zirconium oxide powder, other metal oxide powders such as magnesium oxide (MgO) powder. Thus, an addition of about 0.3 to 3% of magnesium oxide powder can make it possible to increase the fritting temperature by about 150° C.

There can also be used for this same purpose an addition of lanthanum oxide powder ($La_2O_3$) or even powders of other oxides such as yttrium oxide ($Y_2O_3$) or rare earth oxides.

Fritting of the metal oxide powders at a fairly low temperature, for instance at a temperature between 1050° and 1150° C., provides the advantage of being able to work with ovens that are analogous to those commonly used in the dental art.

An elevation of the fritting temperature of the metal oxide particles provides the advantage of being able to impregnate the infrastructure with glass by operating at a higher temperature, which permits a greater diversity in the selection of the glass as will be explained in greater detail below. The glass impregnation of the fritted metal oxide skeleton is effected without having to increase the withdrawal resulting from fritting which is achieved during the first heat treatment. This means that impregnation with the glass must be carried out at a temperature which is at best equal to the fritting temperature during a relatively short period of time which in practice is preferably not in excess of 2 to 4 hours, but which depends on the thickness to be impregnated.

The glass used to effect the impregnation of the skeleton, constituted by the fritted metal oxide powder, must exhibit a number of characteristics.

Although the pores of the fritted metallic oxide skeleton, according to the present invention, can have a size as small as 0.3 micron, it is preferable, in accordance with the invention, that the glass impregnates all of the pores of the skeleton.

To this end, it is preferable that the glass exhibit at the treatment temperature, the characteristics of wetting the fritted metallic oxide skeleton, which means that the surface energy of the glass, at this temperature, must be lower than the surface energy of metal oxide particles.

The wetting character of the glass can be increased in accordance with the present invention by introducing in the composition, for instance, boron oxide, lead oxide or vanadium oxide.

The glass must exhibit preferably, at the considered temperature, a low viscosity, which can be obtained by an appropriate selection of proportions of various oxides, by increasing, for example, the content of boron oxide, lead oxide or lanthanum oxide.

The reactivity of the glass with regard to the metal oxide must be neither too strong, nor too weak. This is obtained by using a glass which contains initially metal oxides such as $Al_2O_3$ and/or $ZrO_2$ in an amount that is slightly lower than, but close to, the saturation of the glass vis-a-vis those metal oxides at the impregnation temperature.

The coefficient of expansion of the glass must, preferably, be lower than, but close to, the coefficient of expansion of the skeleton of fritted metal oxide particles, so as to obtain good resistance against heat shocks for the prosthesis.

The coefficient of expansion of the glass can be adjusted for instance, by adding sodium oxide, potassium oxide or lithium oxide in order to increase it, or by adding silicon oxide or titanium oxide to reduce it.

The impregnation glass can contain a small amount of metal oxides or metals, for instance up to 2%, in order to provide color to the prosthesis and thus alter the color of the fritted metal oxide skeleton.

By selecting an impregnation glass whose index of refraction is more or less close to that of the fritted infrastructure, a more or less transluscent prosthesis is obtained. In this fashion, the index of the refraction of the impregnation glass can be varied in order to obtain different optical effects.

Furthermore, it is important to note that the impregnation glass comprises mainly, a mixture of oxides which, after solidification are provided in a completely amorphous state by being transparent or in a more or less crystalline state by being opalescent.

In order to carry out the impregnation of the fritted metal oxide skeleton with glass, several techniques can be used in accordance with the present invention.

For instance, there can be applied onto the outer surface of the infrastructure of the prosthesis (in other words, on the surface of the prosthesis, whose shape has not been determined by the model of the tooth), a water-based glass paste which, when heated to the appropriate temperature, melts and spreads spontaneously inside the entire volume of the infrastructure by filling all of the pores.

Further, in accordance with the present invention, there can be placed in a cupel, a bed of glass powder, on which the infrastructure is placed and then the whole is heated to the desired temperature. When the glass has melted, it occupies, through capillarity, the entire network of pores in the fritted metal oxide particle infrastructure.

It is preferable that the surface of the prosthesis which comes into contact with the tooth should not contact the melted glass and that the filling of the pores located in the vicinity of this surface is effected by capillarity starting from the interior of the infrastructure mass of fritted metal oxide particles, so that no excess glass remains on the surface, which otherwise would alter its geometry.

It is advantageous to cover the infrastructure comprising the fritted metal oxide particles impregnated with glass by one or more layers of enamel having optical properties and different tints, so as to give the prosthesis the appearance of natural teeth.

In this case, the mass of metal oxide particles that covers the model of the tooth is modeled before fritting, in order to impart to it a shape that provides room necessary for the enamelling that intervenes at the end of the process according to the invention.

It is appropriate to use preferably, as an enamel, a charged glass which has a coefficient of expansion that is slightly lower than that of the infrastructure and whose shaping is effected starting with a powder mixed with water that is sculpted and whose mechanical consolidation is obtained by fritting in liquid phase.

Advantageously, an enamel of the alkali borosilicate type, which contains alumina, is employed.

The present invention also relates to a dental prosthesis obtained by the above described method and which is characterized by the fact that it comprises an infrastructure (or skeleton) obtained by fritting, in solid phase, metal oxide particles and comprising an uninterrupted network, whose interstices are filled with glass.

The following nonlimiting examples are given to illustrate the invention.

EXAMPLE 1

Production of a peripheral cap or crown

Initially, in accordance with conventional techniques the tooth is machined and impressions are taken which make it possible to obtain an initial working model which restores, in positive, the shape of the tooth which is to receive the crown, as well as the shape of the adjacent and opposing teeth.

A second model of the tooth which must receive the crown is produced in a plaster comprising a mixture of 100 g of calcium sulfate hemihydrate and 21 cc of water.

When the plaster, representing the model of the tooth, has set and has dried, it has undergone an expansion of about 0.4%. It is then immersed in a slip, in accordance with the present invention, which comprises 100 g of alumina powder, wherein the average grain size is 3.5 microns, admixed with 13 cc of water containing 0.5 g of cellulose ester, the pH being adjusted to 7.6 by the addition of 0.07 g of citric acid.

Water absorption by the capillaries of the plaster causes an agglomeration of alumina particles onto the surface of the model, according to a thickness which is a function of the period of immersion in the slip, and which can be, for example, about 0.5 to 1 mm or more if necessary.

The thickness of the alumina deposit can be altered either with a brush by bringing some slip to the parts whose thickness is to be increased, or with the aid of a spatula whereby excess deposit can be removed and the edges can be finished.

Therefore, it is possible to proceed easily with sculpting the prosthesis as soon as the alumina deposit has developed essentially the consistency of clay.

Then the plaster model which supports the alumina layer thus produced, is placed in an oven, preferably under vacuum, to facilitate drying, unless it is preferred to let it dry in the open air.

The whole is then placed in a stove where the temperature is initially raised to about 180° C. at a rate of about 1° C. per minute. The temperature is then raised to about 330° C., the entire length of the operation being staged over three to five hours, for example.

The elimination of the constituent water from the plaster and a separation of the model from the alumina infrastructure are thus obtained.

Without removing the ensemble from the stove, the temperature is gradually increased, for example, in about 1 hour, to about 1100° C., a temperature which is maintained for about two hours.

After having allowed cooling to take place, it is noted that the plaster model withdraws substantially, and that the fritted alumina particle infrastructure is sufficiently consolidated so that it can be handled.

The resulting fritting is effected with a withdrawal of 0.3% which is compensated by the expansion of the plaster of the model of the tooth during its setting, taking into account a slack of 0.1% for the placement of the prosthesis.

In order to perform the impregnation in accordance with the present invention using melted glass, the fritted alumina infrastructure is placed inside a cupel on a bed of glass powder whose composition, by weight, is as follows:

| | |
|---|---|
| Silica (SiO$_2$) | 20 g |
| Boron oxide (B$_2$O$_3$) | 19 g |
| Aluminum oxide (Al$_2$O$_3$) | 20 g |
| Lanthanum oxide (La$_2$O$_3$) | 30 g |
| Calcium oxide (CaO) | 5 g |
| Titanium oxide (TiO$_2$) | 4 g |
| Coloring oxides | 2 g |

The glass is gradually heated to a temperature slightly lower than 1100° C. which is maintained for two to three hours, so as to enable the melted glass to penetrate, by capillarity, the alumina particle infrastructure, thereby filling all the pores.

According to the present invention, the crown thus produced is enameled by applying several layers of enamel whose composition, by weight, is as follows:

| | |
|---|---|
| Sodium oxide (Na$_2$O) | 4.6 g |
| Potassium oxide (K$_2$O) | 7.6 g |
| Calcium oxide (CaO) | 1.7 g |
| Aluminum oxide (Al$_2$O$_3$) | 13.9 g |
| Silica (SiO$_2$) | 65.5 g |
| Boron oxide (B$_2$O$_3$) | 6.7 g |

Coloring additives and charges such as tin oxide, silica (quartz), zirconium oxide or aluminum oxide can vary with successive layers.

When the prosthesis in accordance with the present invention is not intended to be enameled, it is clear that the deposit of alumina particles on the plaster model of the tooth, must be given a shape which corresponds to the outer shape that is desired to be imparted to the prosthesis. This is obtained by modeling or sculpting the deposit of alumina particles according to conventional techniques for dental prostheses.

EXAMPLE 2

Production of a peripheral cap or crown

The procedures of Example 1 are repeated, except that the second model of the tooth which must receive the crown is produced using a mixture having the following composition:

| | |
|---|---|
| Refractory charge of Silica (SiO$_2$) or of alumina (Al$_2$O$_3$) | 75 g |
| Magnesium oxide (MgO) | 10 g |
| Ammonium acid phosphate (NH$_4$H$_2$PO$_4$) | 15 g |
| Water | 24 g |

The slip comprises a mixture having the following composition:

| | |
|---|---|
| Aluminum oxide (Al$_2$O$_3$) | 97 g |
| Magnesium oxide (MgO) | 3 g |
| Water | 17 g |
| Polyvinyl alcohol | 0.25 g |

The metal oxides have an average grain size of 8 microns. The pH of the composition is adjusted to 8 by the addition of picric acid.

Fritting is carried out by heating the model of the tooth coated with the layer of metal oxides to a temperature of 1250° C. for 1 hour.

Impregnation of the resulting infrastructure is carried out by contacting it for a period of two hours at a temperature of 1200° C. with a glass having the following composition:

| | |
|---|---|
| Silica (SiO$_2$) | 10 g |
| Boron oxide (B$_2$O$_3$) | 12.5 g |
| Alumina (Al$_2$O$_3$) | 20 g |
| Yttrium oxide (Y$_2$O$_3$) | 20 g |
| Lanthanum oxide (La$_2$O$_3$) | 25 g |
| Titanium oxide (TiO$_2$) | 5 g |
| Calcium oxide (CaO) | 5 g |
| Cerium oxide (CeO) | 2.5 g |

EXAMPLE 3

Production of a peripheral cap or crown

The procedures of Example 1 are repeated and the second model of the tooth is effected using the following composition:

| | |
|---|---|
| Refractory charge of silica (SiO$_2$) or alumina (Al$_2$O$_3$) | 75 g |
| Magnesium oxide | 10 g |
| Ammonium acid phosphate (NH$_4$H$_2$PO$_4$) | 15 g |
| Water | 24 g |

This model is immersed in a slip having the following composition:

| | |
|---|---|
| Alumina (AlO$_3$) | 300 g |
| Water | 20 g |
| Sodium silicate | 0.5 g |

The alumina particles have an average grain size of 20 microns.

Fritting is carried out at a temperature of 1300° C. for about 2 hours.

Impregnation is achieved with a glass having the following composition:

| | |
|---|---|
| Silica (SiO$_2$) | 63 g |
| Alumina (Al$_2$O$_3$) | 14 g |
| Calcium oxide (CaO) | 23 g |

EXAMPLE 4

Production of a peripheral cap or crown

The procedures of Example 1 are repeated and the plaster model of the tooth is immersed in a slip having the following composition:

| | |
|---|---|
| Alumina (Al$_2$O$_3$) | 80 g |
| Zirconium oxide (ZrO$_2$) stabilized with Yttrium | 20 g |
| Water | 15 g |
| Polyvinyl alcohol | 0.1 g |

The alumina particles have an average grain size of about 3.5 microns.

The zirconium oxide particles have an average grain size of 0.5 micron.

The pH is adjusted to 7 by the addition of citric acid.

Fritting is carried out for three hours at a temperature of 1150° C.

Impregnation of the fritted infrastructure is carried out with a glass having the following composition:

| | |
|---|---|
| Silica (SiO$_2$) | 22 g |
| Boron oxide (B$_2$O$_3$) | 15 g |
| Alumina (Al$_2$O$_3$) | 20 g |
| Zirconium oxide (ZrO$_2$) | 2 g |
| Lanthanum oxide (La$_2$O$_3$) | 28 g |
| Calcium oxide (CaO) | 7 g |
| Titanium oxide (TiO$_2$) | 3 g |
| Iron oxide (Fe$_2$O$_3$) | 2 g |
| Cerium oxide (CeO) | 2.5 g |

EXAMPLE 5

Production of a prosthesis involving several teeth simultaneously.

In order to produce a prosthesis that involves several teeth simultaneously, such as a "bridge", the procedures of Examples 1 through 4 are repeated except that a model which includes different teeth that must receive the prosthesis is employed and the deposit of metal oxide particles is sculpted as a function of the shape that is desired for the prosthesis.

In Examples 2 through 5, according to the present invention, enameling can be achieved in successive layers with glasses having the following composition, by weight:

| | |
|---|---|
| Sodium oxide ($Na_2O$) | 4.7 to 4.2 g |
| Potassium oxide ($K_2O$) | 8.2 to 6.8 g |
| Calcium oxide (CaO) | 1.8 to 1.5 g |
| Aluminum oxide ($Al_2O_3$) | 15 to 13 g |
| Silica ($SiO_2$) | 62.8 to 68 g |
| Boron oxide ($B_2O_3$) | 7.5 to 6.5 g |

EXAMPLE 6

Production of a partial reconstitution piece

These pieces which are usually known as "inlay" and "onlay" are used to fill a cavity which is carried out by stripping the tooth.

To this end, an impression is taken which makes it possible to reconstitute a positive model of the tooth made of plaster or another porous material. Using a brush, for instance, the slip is deposited in the cavity of the model in such a way that the latter is filled with a sufficient quantity of metal oxide particles that is sculpted to restore the missing piece of the tooth.

The procedures outlined in the previous examples can be repeated although in this situation it is generally not necessary to cover the resulting prosthesis with a layer of enamel.

What is claimed is:

1. A method for manufacturing ceramic dental prosthesis comprising
    molding a model of a tooth that is to receive said prosthesis from a molding mass that slightly expands linearly on solidification,
    preparing a slip comprising an aqueous suspension of metal oxide particles to which has been added a suspension stabilization agent;
    contacting said model of said tooth with said slip until a layer of agglomerated metal oxide particles has been achieved,
    imparting to said layer of agglomerated metal oxide particles an outer shape desired for an infrastructure of said prosthesis,
    baking said model of said tooth coated with said metal oxide based infrastructure to effect initially a dehydration of said model of said tooth thereby causing withdrawal of said model from said infrastructure,
    slightly solid phase fritting the metal oxide based infrastructure to produce a binding between said metal oxide particles without causing a substantial volumetric reduction of said infrastructure, and then
    impregnating said infrastructure with glass at a temperature such that all pores of said infrastructure are filled with said glass, thereby producing said prosthesis.

2. The method of claim 1 wherein said model of said tooth expands linearly between about 0.1 to 0.4 percent on soldification.

3. The method of claim 1 wherein said molding mass is a mineral charge free calcium sulfate hemihydrate.

4. The method of claim 1 wherein said slip contains about 0.05 to about 0.5 weight percent of said metal oxide particles and said suspension stabilization agent is polyvinyl alcohol, an acrylic acid, a cellulose ester or sodium silicate.

5. The method of claim 1 which includes degassing said slip, prior to placing said model of said tooth in contact therewith, by submitting said slip to ultrasonics in a vacuum.

6. The method of claim 1 wherein said fritting of said infrastructure is carried out at a temperature of about 1050° C. to 1150° C. when said metal oxide particles are alumina having an average size of about 3.5 microns.

7. The method of claim 1 wherein fritting of said infrastructure is carried out at a temperature of about 1250° C. when said metal oxide particles are alumina having an average size of about 8.5 microns.

8. The method of claim 1 wherein said fritting of said infrastructure is carried out at a temeperature of about 1300° C. to 1400° C. when said metal oxide particles are alumina having an average size of about 20 microns.

9. The method of claim 1 wherein said metal oxide particles have a specific surface of about 1 to 5 $m^2$/gram.

10. The method of claim 1 wherein said glass employed to impregnate said infrastructure has a surface energy at said impregnation temperature lower than a surface energy of said infrastructure after said fitting.

11. The method of claim 1 wherein said glass contains lead oxide, boron oxide or vanadium oxide in an amount sufficient to increase the wettability of said glass.

12. The method of claim 1 wherein said glass comprises same metal oxides employed in said infrastructure wherein said metal oxides are present in amount slightly less than a saturation of said glass relative to said metal oxides at said impregnation temperature.

13. The method of claim 1 wherein said glass has a coefficient of expansion lower than a coefficient of expansion of said infrastructure.

14. The method of claim 1 wherein said glass contains up to 2 weight percent of a color-imparting metal oxide.

15. The method of claim 1 wherein said glass is a mixture of oxides which after solidification provides an essentially amorphous mass which is transparent or provides an essentially crystalline mass which is opalescent.

16. The method of claim 1 wherein said glass has an index of refraction different from an index of refraction of said infrastructure.

17. The method of claim 1 wherein to said slip comprising said aqueous suspension of metal oxide particles of pH control agent has been added.

18. The method of claim 1 wherein said molding mass comprises silicon oxide or aluminum oxide together with a binding agent.

19. The method of claim 18 wherein said binding agent is sodium silicate, ethyl silicate, ammonium sulfate, aluminum phosphate or sodium phosphate.

20. The method of claim 1 which includes adjusting pH of said slip to about 7 to 8 by addition thereto of a pH control agent.

21. The method of claim 20 wherein said pH control agent is citric acid.

22. The process of claim 1 wherein said model of said tooth coated with said metal oxide based infrastructure is baked initially at a temperature which is raised slowly at a rate of 1° C./minute up to a temperature of about 350° C. and thereafter raising the temperature to at least equal to about 1050° C. for a time sufficient to effect said fritting of said metal oxide based infrastructure.

23. The method of claim 22 wherein during said fritting said infrastructure undergoes a withdrawal from said model of said tooth of less than 0.4% so as to correspond to a percent expansion of said model of said tooth on solidification of said molding mass.

24. The method of claim 1 wherein an outer surface of said prosthesis is coated with an enamel compatible with said glass employed to impregnate said infrastructure, said enamel having a coefficient of expansion close to said glass.

25. The method of claim 24 wherein said enamel has a coefficient of expansion lower than said glass.

26. The method of claim 24 wherein said enamel is an alkali borosilicate containing alumina.

27. The method of claim 1 wherein said metal oxide particles are alumina particles.

28. The method of claim 27 wherein said metal oxide particles also include magnesium oxide, lanthanum oxide or rare earth metal oxide.

29. The method of claim 27 wherein said metal oxide particles also include zirconium oxide particles.

* * * * *